United States Patent [19]

Juby et al.

[11] Patent Number: 4,457,932

[45] Date of Patent: Jul. 3, 1984

[54] ANTI-ULCER AGENTS

[75] Inventors: Peter F. Juby, Jamesville; Thomas W. Hudyma; Douglas G. Colton, both of Manlius, all of N.Y.

[73] Assignee: Bristol-Myers Company, New York, N.Y.

[21] Appl. No.: 516,026

[22] Filed: Jul. 22, 1983

[51] Int. Cl.³ .......................................... A61K 31/505
[52] U.S. Cl. .................................................. 424/251
[58] Field of Search ...................................... 424/251

[56] References Cited

U.S. PATENT DOCUMENTS

| | | | |
|---|---|---|---|
| 3,072,485 | 1/1963 | Reynolds et al. | 96/115 |
| 3,585,198 | 6/1971 | Meszaros et al. | 260/251 |
| 3,855,216 | 12/1974 | Kaminsky et al. | 260/243 R |
| 3,862,141 | 1/1975 | Klutchko et al. | 260/335 |
| 3,929,787 | 12/1975 | Yale | 260/251 |
| 3,960,847 | 6/1976 | Yale | 260/240 K |
| 4,014,881 | 3/1977 | Kadin et al. | 260/256.4 |
| 4,041,163 | 8/1977 | Bindra | 424/251 |
| 4,105,764 | 8/1978 | Alexander | 424/248.54 |
| 4,105,766 | 8/1978 | Alexander | 424/251 |
| 4,122,274 | 10/1978 | Juby | 544/282 |
| 4,141,979 | 2/1979 | Bindra | 424/251 |
| 4,152,448 | 5/1979 | Wardell | 424/283 |
| 4,209,620 | 6/1980 | Juby | 544/252 |
| 4,236,004 | 11/1980 | Scotese et al. | 544/279 |
| 4,310,526 | 1/1982 | Doria et al. | 424/248.55 |

FOREIGN PATENT DOCUMENTS 2063862  6/1981  United Kingdom ............... 424/251

OTHER PUBLICATIONS

Gastroenterology 77: 433-443, 1979, Robert et al.
Advances in Prostaglandin & Thromboxane Research, vol. 2, 1976, Robert.
Scand. J. Gastroenterology 67: 223-227, 1981, Robert.
Chemical & Pharmaceutical Bulletin, vol. 22: 1974, Okamoto et al.
J. Chem. Soc. C: 2735, 1971.
J. Amer. Chem. Soc. 74: 5491, 1952.
J. Org. Chem., vol. 33, No. 8, Aug. 1968, Shur et al.
Arzneimittel-Forschung 22: 815-952, Meszaros et al., 1972.
Tetrahedron Lett., No. 12, p. 1019, 1975.

Primary Examiner—Frederick E. Waddell
Attorney, Agent, or Firm—David M. Morse

[57] ABSTRACT

Disclosed is a method of using certain substituted 3-(1H-tetrazol-5-yl)-4H-pyrido[1,2-a]pyrimidin-4-one compounds, previously known as having antiallergy activity, for the treatment of peptic ulcer disease and other gastrointestinal diseases characterized by inflammation and necrosis.

20 Claims, No Drawings

ANTI-ULCER AGENTS

BACKGROUND OF THE INVENTION

1. Field of the Invention

This invention relates to a method of treating peptic ulcer disease in mammalian hosts by administering a substituted 3-(1H-tetrazol-5-yl)-4H-pyrido[1,2-a]pyrimidin-4-one compound.

2. Description of the Prior Art

The recent successful introduction of the histamine H$_2$-receptor antagonist, cimetidine, for the treatment of peptic ulcer disease has renewed interest in developing new antiulcer compounds which might have even greater potency and specificity and/or reduced side effects. The literature indicates significant progress in developing improved inhibitors of gastric acid secretion which work as H$_2$-receptor antagonists (e.g. ranitidine and etintidine) or by mechanisms other than competitive H$_2$-receptor antagonism. Another interesting approach to antiulcer therapy involves the search for so-called cytoprotective agents which have the property of protecting the gastrointestinal tract from damage induced by noxious agents. To date, the main studies of this cytoprotective effect have been carried out with prostaglandins, although a recent U.K. Patent Application No. 2,063,862A claims that the non-prostaglandin compound 5,6,7,8-tetrahydro-N-(5-tetrazolyl)-4-oxo-4H-pyrimido[2,1-b]benzothiazole-3-carboxamide also has been found to possess cytoprotective effects. The term "cytoprotective" has been defined by A. Robert (*Gastroenterology*, 77: 433–443, 1979; *Advances in Prostaglandin and Thromboxane Research* 2: 507, 1976; *Scand. J. Gastroent.* 16: 223–227, 1981) as the property of a compound to protect the mucosa of the stomach and intestine from becoming inflamed and necrotic when this mucosa is exposed to noxious agents. While the mechanism of cytoprotection is not yet known, cytoprotective effects by definition are independent of any antisecretory activity that a compound may also possess.

The substituted 3-(1H-tetrazol-5-yl)-4H-pyrido[1,2-a]pyrimidin-4-one compounds of the present invention have been previously disclosed in U.S. Pat. Nos. 4,122,274 and 4,209,620 as having antiallergery activity. There is no disclosure in these patents, however, that these compounds also have potent antiulcer activity.

With respect to other literature relating to the compounds of the present invention, no examples of tetrazol-5-yl-4H-pyrido[1,2-a]pyrimidin-4-ones have been located by the present inventors. Numerous examples of the pyrido[1,2-a]pyrimidine ring system, however, are known, including many 4-oxo derivatives.

U.S. Pat. No. 3,585,198 reviews some of the literature of the pyrido[1,2-a]pyrimidines and discloses compounds of the general formula

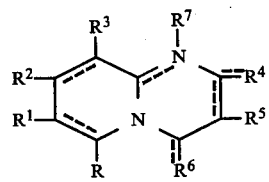

where R, R$^1$, R$^2$ and R$^3$ may be hydrogen, alkyl, alkoxy, halogen, nitro or amino, R$^4$ is hydrogen, alkyl, aralkyl, aryl, =O, alkoxy, halogen or hydroxy, R$^5$ is hydrogen, halogen, a —CH$_2$—OH group, a carboxylic acid or carboxylic acid derivative group, R$^6$ is hydrogen, alkyl, aralkyl, aryl, =O, alkoxy, halogen, or hydroxy and R$^7$ is hydrogen, alkyl, aryl or alkyl, and where the dotted lines represent optional double bonds. The disclosed compounds are said to exhibit analgesic, antipyretic and narcosis potentiating effects.

U.S. Pat. No. 3,929,787 discloses 2-aryl-9-alkyl-4H-pyrido[1,2-a]pyrimidin-4-one compounds of the formula

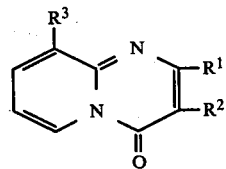

where R$^1$ is phenyl or substituted phenyl, R$^2$ is hydrogen or alkyl and R$^3$ is alkyl. These compounds are reported to be intermediates in preparing the corresponding 6,7,8,9-tetrahydro derivatives which possess central nervous system depressant activity.

U.S. Pat. No. 3,072,485 discloses inter alia compounds of the formula

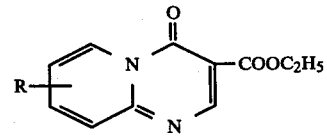

where R is hydrogen, bromo, chloro, iodo or methyl. The compounds are used as photogenic sensitizers.

Compounds of the formula

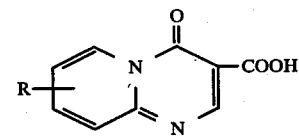

wherein R is hydrogen, 9-methyl or 8-methyl are disclosed by Okamoto, et al. in *Chem. Pharm. Bull.* (Tokyo), 22, 243 (1974). No pharmacological utility for the compounds is indicated.

U.S. Pat. No. 3,960,847 discloses inter alia 9-substituted pyrido[1,2-a]pyrimidines of the formula

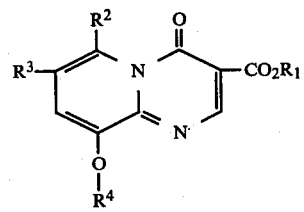

where R$^1$ is hydrogen or C$_1$–C$_4$ alkyl, R$^2$ and R$^3$ are hydrogen, C$_1$–C$_4$ alkyl, CF$_3$, F, Cl or Br and R$^4$ is inter alia an alkyl radical substituted by a phenyl or substituted phenyl radical, such as benzyl, substituted benzyl, phenethyl or substituted phenethyl. The compounds are said to have both central nervous system and hypotensive activities.

J. K. Landquist has described in *J. Chem. Soc.*(C), 2735 (1971) the preparation of the carboxamide compound of the formula

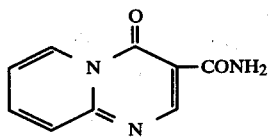

by treatment of the corresponding ethyl ester with ammonium hydroxide in ethanol. No pharmacological utility is given for the disclosed carboxamide.

Preparation of the cyano derivatives of the formula

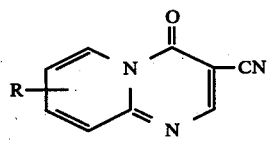

where R is hydrogen, 6-methyl or 9-methyl is disclosed in *J. Amer. Chem. Soc.* 80: 3066 (1958). No pharmacological utility for the compounds is indicated.

Other references to the chemistry of pyrido[1,2-a]pyrimidinones include *J. Amer. Chem. Soc.* 74: 5491 (1952), *J. Org. Chem.* 33: 3015 (1968), *Arzneim-Forsch.* 22: 815 (1972) and *Tetrahedron Lett.* (12): 1019 (1975).

A number of structurally unrelated heterocycle compounds have been disclosed as having antiallergy and/or antiulcer activity. Representative of literature references disclosing such compounds are the following.

1. U.S. Pat. No. 4,310,526 discloses substituted 6,7-methylene pyrido[1,2-a]pyrimidines of the formula

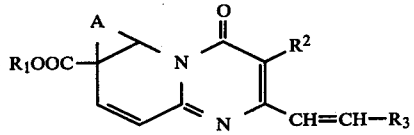

wherein A completes a bond, thereby providing a double bond between the 6- and 7-carbon atoms, or A represents a —CH₂— group, thereby providing a cyclopropane ring fused to the pyrido ring at the 6,7-position; R₁ represents a hydrogen atom or a C₁–C₁₂ alkyl group which is unsubstituted or substituted by a

group, wherein each of R₄ and R₅ independently represents a hydrogen atom or a C₁–C₁₀ alkyl group, or R₄ and R₅, taken together with the nitrogen atom to which they are attached, form a N-pyrrolidinyl, piperidino or morpholino group; R₂ represents a hydrogen atom or a C₁–C₆ alkyl group or a C₃— or C₄—alkenyl group; R₃ represents (a) a furyl, thienyl or pyridyl group each of which is unsubstituted or substituted by a methyl group; or (b) a group of the formula

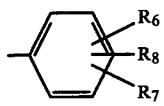

wherein each of R₆, R₇ and R₈ independently represents a hydrogen or halogen atom, a hydroxy group, a C₁–C₄ dialkylamino group, a group —CF₃ or a group —R₉ or —OR₉, where R₉ represents a C₁–C₆ alkyl or C₃— or C₄—alkenyl group, and pharmaceutically acceptable salts thereof as having anti-allergic, antiulcer and anti-diabetic activities.

2. U.K. Patent Application No. 2,063,862A discloses antiallergic and antiulcer 1-oxo-1H-thiazolo[3,2-a]-pyrimidine-2-carboxamides of the formula

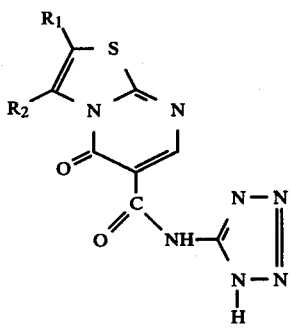

and their pharmaceutically acceptable salts, wherein R₁ and R₂ taken separately are each hydrogen or C₁₋₅ alkyl; and R₁ and R₂ taken together are alkylene of 3–9 carbon atoms or phenylalkylene of 9–11 carbon atoms, with the proviso that the ring so formed is between 5- and 8-membered.

3. U.S. Pat. No. 3,855,216 discloses substituted pyrano[3,2-c]-[1,2]benzothiazine 6,6-dioxides of the formula

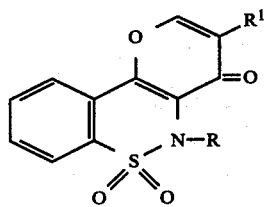

wherein R represents hydrogen and (lower)alkyl and R¹ represents (lower) alkyl, formyl and hydroxymethyl and the corresponding aldehyde thiosemicarbazone derivatives thereof as having antisecretory and antiallergy activity.

4. U.S. Pat. No. 3,862,141 discloses 1-substituted 1,2,3,4-tetrahydroxanthen-9-one compounds of the formula

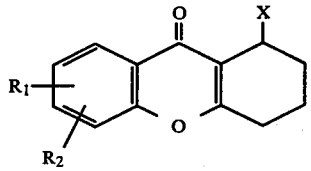

wherein X is hydroxy or carbonyl oxygen, $R_1$ and $R_2$ are hydrogen, halogen, (lower)alkyl, (lower)alkoxy or hydroxy, or $R_1$ and $R_2$ taken together form another ring such as benzene, as antisecretory and antiallergy agents.

5. U.S. Pat. No. 4,014,881 discloses 1-oxo-1H-6-substituted pyrimido[1,2-a]quinoline-2-carboxylic acid derivatives of the formula

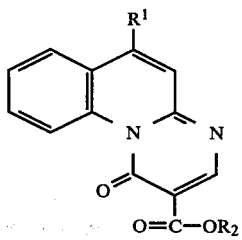

wherein $R_1$ is $C_1$–$C_2$ alkoxy or piperidino and $R_2$ is hydrogen or $C_1$–$C_4$ alkyl and pharmaceutically acceptable salts as antiulcer agents.

6. U.S. Pat. No. 4,041,163 discloses N-(5-tetrazolyl)-4-oxo-4H-pyrimido[2,1-b]benzothiazole-3-carboxamides of the formula

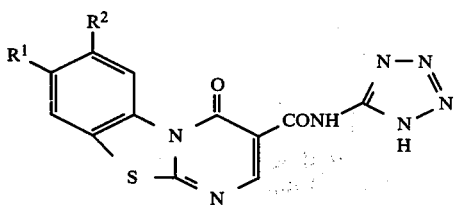

wherein $R^1$ is hydrogen, $C_1$–$C_3$ alkyl, $C_1$–$C_3$ alkoxy, hydroxy, chloro, fluoro, trifluoromethyl, nitro, amino or methylthio and $R^2$ is hydrogen, $C_1$–$C_3$ alkyl, $C_1$–$C_3$ alkoxy, hydroxy, chloro, fluoro or methylthio, or $R_1$ and $R_2$ when taken together are methylenedioxy or ethylenedioxy, and pharmaceutically acceptable salts thereof as antiallergy agents.

7. U.S. Pat. No. 4,236,004 discloses 2-alkylsulfonyl-7,8-dihydro-5-hydroxy-7-oxo-pyrido[2,3-d]pyrimidine-6-carboxylic acid compounds of the formula

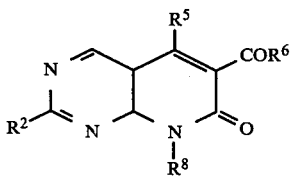

wherein $R^2$ is hydrogen, hydroxy, $C_1$–$C_6$ alkyl, $C_1$–$C_6$ alkylthio, phenyl, 4-methoxyphenyl, 4-chlorophenyl, 1-pyrrolidinyl or methylphenylamino; $R^5$ is hydroxy, $C_1$–$C_6$ alkylamino, 2-hydroxyethylamino, 2-alkoxyethylamino, dialkylamino where each alkyl is $C_1$–$C_6$, 4-methyl-1-piperazinyl, 4-morpholinyl or 1-pyrrolidinyl when $R^2$ is other than alkylthio and $R^8$ is other than alkyl or -NH$_2$ when $R^8$ is other than alkyl; $R^6$ is $C_1$–$C_6$ alkoxy, amino, mono- and dialkylamino where each alkyl group is $C_1$–$C_6$, 2-hydroxyethylamino, 2-alkoxyethylamino of 3–8 carbons or 2-(dialkylamino)ethylamino in which each alkyl group is $C_1$–$C_6$; and $R^8$ is hydrogen, $C_1$–$C_6$ alkyl, 2-alkoxyethyl of 3–8 carbons, allyl, propargyl, phenyl, 4-methoxyphenyl, 4-chlorophenyl, benzyl, 4-methoxybenzyl, 4-chlorobenzyl, 4-(4-morpholinyl)-phenyl or piperonyl as having anti-secretory and antiallergy activity.

8. U.S. Pat. No. 4,141,979 discloses tetrazolo[a]quinazol-5-ones of the formula

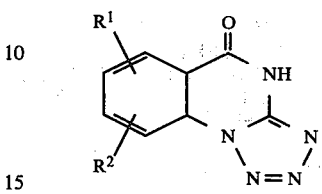

wherein each of $R^1$ and $R^2$ is selected from hydrogen, $C_1$–$C_4$ alkyl, $C_1$–$C_4$ alkoxy, $C_1$–$C_4$ alkanoyloxy, benzyloxy, hydroxy, trifluoromethyl, sulfonamido and halo, or $R^1$ and $R^2$ when taken together are methylenedioxy or ethylenedioxy, as antiallergy agents and as antiulcer agents.

9. U.S. Pat. No. 4,105,766 discloses certain carboxylic acids and esters of the formula

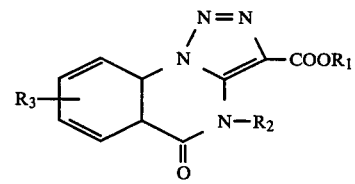

wherein $R_1$ is hydrogen, lower alkyl or pivaloyloxymethyl; $R_2$ is hydrogen, methyl, ethyl, lower-alkenyl or cyclopropylmethyl; and $R_3$ is hydrogen, 7- or 8-methyl, 7- or 8-halo or 7-nitro as having antiallergy activity. This same patent, however, (and also U.S. Pat. No. 4,105,764) discloses that the above compounds have no antiulcer (antisecretory) activity whereas the corresponding compounds having an amide group at the 3-position have antiulcer activity but not antiallergy activity.

SUMMARY OF THE INVENTION

The method of the present invention resides in the induction of cytoprotective activity in a mammalian host and most preferably in the treatment of gastrointestinal diseases characterized by inflammation and necrosis such as peptic ulcer, gastritis, inflammatory bowel disease, Crohn's disease, ulcerative colitis, coeliac disease, etc. by administering to a mammalian host a substituted 3-(1H-tetrazol-5-yl)-4H-pyrido[1,2-a]pyrimidin-4-one compound having the formula

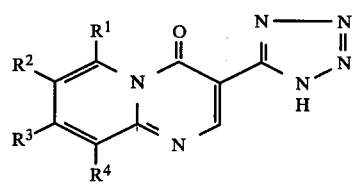

wherein $R^1$, $R^2$, $R^3$ and $R^4$ which may be the same or different are each hydrogen, halogen or (lower)alkyl, or wherein $R^3$ and $R^4$ when taken together are $(CH_2)_n$ in which n is 3, 4 or 5, or a pharmaceutically acceptable salt thereof, with the proviso that $R^1$, $R^2$, $R^3$ and $R^4$ may not all be hydrogen.

DETAILED DESCRIPTION

The compounds of Formula I for use in the method of the present invention may be prepared by the procedures disclosed in U.S. Pat. Nos. 4,122,274 and 4,209,620, the disclosures of which are incorporated herein by reference.

The $R^1$, $R^2$, $R^3$ and $R^4$ substituent groups disclosed above may be further defined as follows:

(a) Halogen includes chlorine, bromine, fluorine and iodine, and is most preferably chlorine;

(b) Lower(alkyl) includes both straight and branched chain saturated aliphatic hydrocarbon radicals having from 1-4 carbon atoms inclusive, i.e. methyl, ethyl, n-propyl, isopropyl, n-butyl, isobutyl, t-butyl and sec-butyl, and is more preferably methyl, ethyl, n-propyl or n-butyl, and most preferably methyl, ethyl or n-propyl; and (c) $(CH_2)_n$ represents a saturated five, six or seven membered monocyclic hydrocarbon radical fused to the A ring of the pyrido[1,2-a]pyrimidine ring system, e.g.

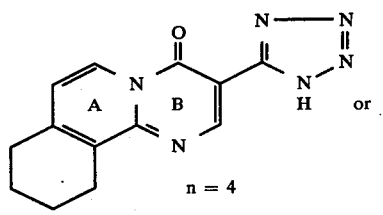

n = 4

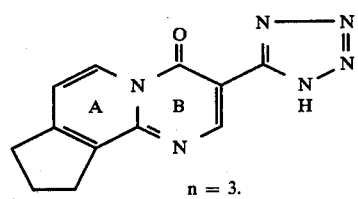

n = 3.

A preferred embodiment of the present invention comprises use of compounds of Formula I wherein at least two of the $R^1$, $R^2$, $R^3$ and $R^4$ substituents are hydrogen.

Another preferred embodiment comprises use of compounds of the formula

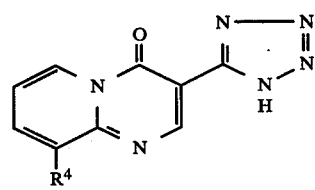

wherein $R^4$ is halogen or (lower)alkyl including pharmaceutically acceptable salts thereof. Especially preferred compounds of this type are those wherein $R^4$ is chloro, methyl, ethyl, n-propyl or n-butyl. A most preferred embodiment is the compound wherein $R^4$ is methyl and the pharmaceutically acceptable salts thereof.

Another preferred embodiment comprises use of compounds of the formula

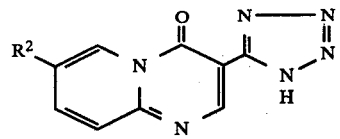

wherein $R^2$ is halogen or (lower)alkyl including pharmaceutically acceptable salts thereof. Especially preferred compounds of this type are those wherein $R^2$ is chloro, methyl, ethyl or n-butyl.

Another preferred embodiment comprises use of compounds of the formula

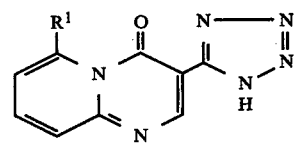

wherein $R^1$ is halogen or (lower)alkyl including pharmaceutically acceptable salts thereof. An especially preferred compound of this type is the compound wherein $R^1$ is methyl and the pharmaceutically acceptable salts thereof.

Another preferred embodiment comprises use of compounds of the formula

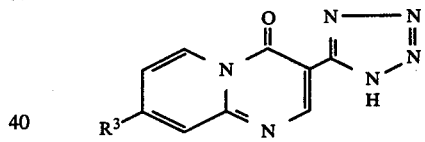

wherein $R^3$ is halogen or (lower)alkyl including pharmaceutically acceptable salts thereof. An especially preferred compound of this type is the compound wherein $R^3$ is methyl and the pharmaceutically acceptable salts thereof.

Another preferred embodiment comprises use of compounds of the formula

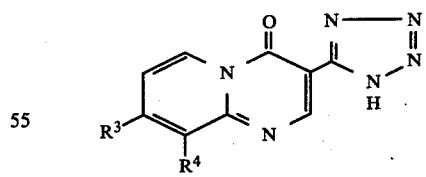

wherein $R^3$ and $R^4$ when taken together represent $(CH_2)_n$ in which n is 3, 4 or 5 including pharmaceutically acceptable salts thereof. An especially preferred compound of this type is the compound wherein n is 4 and the pharmaceutically acceptable salts thereof.

Another preferred embodiment comprises use of compounds of the formula

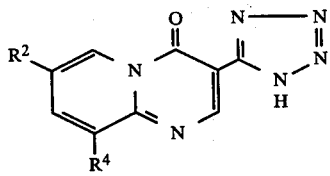

wherein $R^2$ and $R^4$ are each independently (lower)alkyl. An especially preferred compound of this type is the compound wherein $R^2$ and $R^4$ are both methyl and the pharmaceutically acceptable salts thereof.

Since the compounds used in the method of the present invention are amphoteric in nature, they can be converted to salts of either acids or bases by the methods disclosed in U.S. Pat. No. 4,122,274. The term "pharmaceutically acceptable salts" as used herein refers to nontoxic salts formed from such acids as hydrochloric, hydrobromic, hydroiodic, nitric, sulfuric, phosphoric, acetic, lactic, citric, tartaric, oxalic, succinic, maleic, gluconic, ascorbic or p-toluene sulfonic or such bases as ammonia, primary amines such as n-propylamine, n-butylamine, ethanolamine, ethylenediamine, cyclohexylamine, benzylamine, ethylamine, octylamine or tris(hydroxymethyl)aminomethane, secondary amines such as diethanolamine, tertiary amines such as triethanolamine, N-methylpyrrolidine, N-methylmorpholine, 1,5-diazabicyclo[4,3,0]-5-nonene and metal compounds such as sodium hydroxide, potassium hydroxide, ammonium hydroxide, sodium ethoxide, potassium methoxide, magnesium hydroxide, calcium hydroxide or aluminum hydroxide.

Those skilled in the art will appreciate that the compounds represented by Formula I contain a tautomeric hydrogen atom and the compounds are thus capable of existing in the 1H-tetrazol-5-yl form (see Formula I$_a$ below) and the 2H-tetrazol-5-yl form (Formula I$_b$ below).

pancreas against necrosis caused by various noxious agents.

The compounds may be administered either as individual therapeutic agents or as mixtures with other therapeutic agents. They may be administered alone but are generally administered in the form of pharmaceutical compositions, i.e. mixtures of the active agents with suitable pharmaceutical carriers or diluents. The compounds or compositions may be administered orally, parenterally or by rectal suppository, but are most preferably administered in oral dosage forms.

The nature of the pharmaceutical composition and the pharmaceutical carrier or diluent will, of course, depend on the desired route of administration. Thus, for example, oral compositions may be in the form of tablets or capsules and may contain conventional excipients such as binding agents (e.g. syrup, acacia, gelatin, sorbitol, tragacanth or polyvinyl pyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) or wetting agents (e.g. sodium lauryl sulfate). Oral liquid preparations may be in the form of aqueous or oily suspensions, solutions, emulsions, syrups, elixers, etc. or may be presented as a dry powder for reconstitution with water or other suitable vehicle before use. Such liquid preparations may contain conventional additives such as suspending agents, flavoring agents, diluents or emulsifying agents. For parenteral administration, solutions or suspensions with conventional pharmaceutical vehicles may be employed.

The compounds of Formula I (including pharmaceutically acceptable salts thereof) or pharmaceutical compositions thereof may be administered to mammalian hosts in need of such treatment in doses ranging from about 0.05 milligram to about 200 milligrams per kilogram of body weight per day. They may be administered in a single dose or a plurality of divided doses. These particular dosage values are illustrative only,

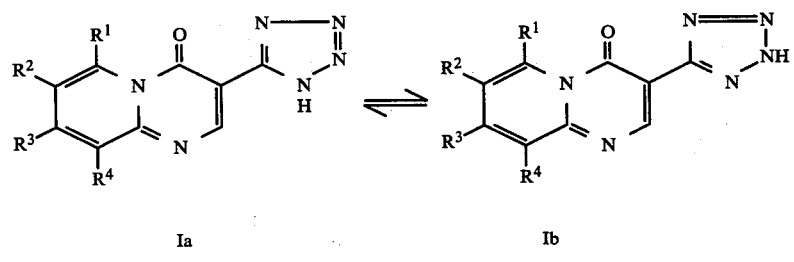

Ia        Ib

This invention embraces both forms, but for the sake of convenience, structure Ia has been arbitrarily selected to describe the present compounds.

In accordance with the method of the present invention, the compounds of Formula I and the pharmaceutically acceptable salts thereof are effective as cytoprotective agents in treating various mammalian gastrointestinal diseases characterized by inflammation and necrosis such as gastric ulcer, gastritis, duodenal ulcer, inflammatory bowel disease, Crohn's disease, ulcerative colitis, coeliac disease, etc. They are of particular value in the treatment of peptic ulcer disease where they not only accelerate healing of such ulcers but also prevent ulcer formation. In addition to their use as cytoprotective agents in treatment of gastrointestinal disease (e.g. peptic ulcer), the Formula I compounds are useful in protecting other organs such as the liver, colon and however, and the physician of course will ultimately determine the dosage most suitable for a particular host animal on the basis of such factors as age, weight, the particular disease being treated, severity and locus of the disease and the particular agent to be administered.

The effectiveness of the compounds of Formula I as cytoprotective agents was determined by an ethanol-induced ulcer model in the rat. This model is a modification of the procedure described by A. Robert in *Scand. J. Gastroenterology* 16: (Suppl. 67): 243 (1981). This model which screens for cytoprotective compounds is based on the ability of 100% ethanol to produce gastric ulcers (primarily in the fundic region of the stomach) in rats in a dose-related manner. Further details of the model are described below.

Ethanol-Induced Ulcer Model

Adult male Long-Evans rats weighing 275-300 grams (Blue Spruce Farm, Alton, N.Y.) are used. Animals are housed individually in stainless steel cages with wire-mesh bottoms. The housing battery is arranged into six groups of five each, individually numbered from rat number 1, group 1 to rat number 5, group 6. Food and water are removed 24 and 18 hours, respectively, prior to testing. On the following day animals receive the test compound either p.o., s.c. or i.p. 30 minutes or more before administration of 100% ethanol (3.0 ml/kg) by gavage. Sixty minutes later the animals are sacrificed by administration of T-61 (Hoechst), 0.2 ml i.p.

An abdominal incision is made and, after clamping the esophagus just above the esophageal sphincter with tweezers, the stomach is carefully lifted from the abdominal cavity. Two cuts are made approximately ½" below the pyloric valve and ½" above the esophageal sphincter, and the stomach removed and set aside. This step is very rapid (2-3 seconds) and no loss of gastric contents is apparent. The size of the stomach including contents is noted as small, medium or large. Stomachs are cut open along the lesser curvature and the contents expressed into graduated centrifuge tubes.

Under these conditions, ethanol produces prominent macroscopic lesions in the corpus, but gross macroscopic changes are only very rarely observed in the forestomach. An occasional control animal shows some degree of redness or hyperemia and/or small petechiae in the forestomach, but never lesions characteristic of fundic damage. In addition, absence of the forestomach allows the remaining stomach to lie flat on a surface for photography and examination without undue stretching of the tissue. For these reasons, the forestomach (along with nongastric tissue) is removed.

The remaining corpus and antrum are rinsed in water and placed flat in a standard position. The tissue is photographed with a Polaroid close-up camera and scoring of lesions is done from this permanent record. Each photograph includes a reference scale in mm. Two scoring systems are used. For screening purposes each stomach is graded on a scale of 0 to 3 as described below:

| Score | Incidence of Visible Lesions |
|-------|------------------------------|
| 0     | None                         |
| 0.5   | Minimal                      |
| 1.0   | Low                          |
| 2.0   | Moderate                     |
| 3.0   | Severe                       |

A control group of rats would have a score of approximately 10 (5×2) on the average, although rat-to-rat variability is high.

Where more precise data are needed, e.g, in determining the $ED_{50}$ for a compound, the total lesion area in mm is measured. Barely visible spots (petechiae) are scored as 1 mm each. For each treatment group, an average score is calculated. From this, the percent inhibition of lesion formation, I, is calculated as:

I = Lesion Score (controls)-Lesion Score(treated) $\times$ 100 Lesion Score(controls)

In dose-response studies, the $ED_{50}$ (dose at which 50% inhibition of lesion formation occurs) is determined by probit analysis according to Finney.

Certain additional data are obtained routinely. Gastric juice samples are centrifuged and total volume, contents of solids, and mucus are estimated to the nearest 0.1 ml. The color of the gastric juice is noted: clear (C), amber (A), yellow (Y), bloody (B). After determining gastric juice pH, samples are assayed for Na and K contents.

Comparisons between groups are done using Student's t-test.

In rare instances, the data from an animal will be discarded if, e.g., feces are found in the stomach, or if there is evidence that the animal never received the ethanol in the stomach.

Both $PGE_2$ and sucralfate are active in this model, with oral $ED_{50}$'s of 24 μg/kg and 21 mg/kg, respectively. Cimetidine is also active ($ED_{50}$=235 mg/kg, but at doses much higher than necessary to inhibit acid secretion, and thus is not considered cytoprotective.

Results

Test results for certain representative compounds of the present invention by p.o. route of administration are shown in the Table below. The results are given as percent inhibition of lesion formation after administration of the indicated dose of test compound.

| Antiulcer Activity of Substituted 3-(1H—tetrazol-5-yl)-4H—pyrido[1,2-a]pyrimidin-4-ones | | |
|---|---|---|
| | Antiulcer Activity | |
| Compound | Dose, mg/kg p.o. | % Inhibition |
| 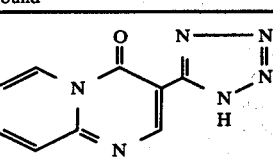 | 12.6 | 93 |
| 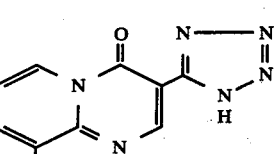 | 30 | 68 |
|  (potassium salt) | 30 | *88 |
| 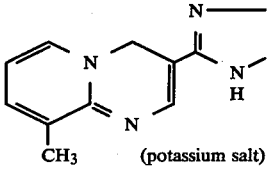 | 30 | 75 |
| 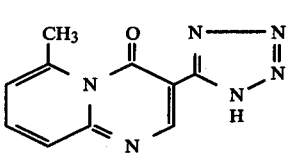 | 30 | 79 |

-continued

Antiulcer Activity of Substituted 3-(1H—tetrazol-5-yl)-4H—pyrido[1,2-a]pyrimidin-4-ones

| Compound | Dose, mg/kg p.o. | % Inhibition |
|---|---|---|
| $C_4H_9$ substituted pyrido[1,2-a]pyrimidin-4-one with tetrazolyl | 30 | 54 |
| Cl substituted pyrido[1,2-a]pyrimidin-4-one with tetrazolyl | 12.6 | 93 |
| $CH_3$, $CH_3$ disubstituted pyrido[1,2-a]pyrimidin-4-one with tetrazolyl | 30 | 92 |
| $CH_3$ substituted pyrido[1,2-a]pyrimidin-4-one with tetrazolyl | 30 | 70 |
| $C_2H_5$ substituted pyrido[1,2-a]pyrimidin-4-one with tetrazolyl | 50 | 96 |
| $C_3H_7$ substituted pyrido[1,2-a]pyrimidin-4-one with tetrazolyl | 30 | 77 |
| $C_4H_9$ substituted (reduced) with tetrazolyl | 50 | 41 |
| Cl substituted (reduced) with tetrazolyl | 24 | 85 |

*$ED_{50}$ (mg/kg) = 0.3

The compound of Formula I wherein $R^4$ is methyl and $R^1$, $R^2$ and $R^3$ are each hydrogen was also tested in several other ulcer models. This compound was inactive when dosed at 100 mg/kg p.o. in an aspirin-stress gastric ulcer model in rats, and was also inactive when dosed seven times over 30 hours (40 mg/kg, p.o.) in a cysteamine-induced duodenal ulcer model in rats. The compound was found to block gastric secretion in the conscious gastric fistula rat, but the oral $ED_{50}$ was a relatively poor 27 mg/kg. The results in the above models are probably indicative of the lack of significant anti-secretory activity in the compound of the present invention.

When tested against HCl-induced gastric lesions in the rat, the above-mentioned compound was active with an $ED_{50}$ of 20.8 mg/kg p.o. Since this model like the ethanol-induced ulcer model is most indicative of cytoprotective activity, the activity in this test is consistent with the compounds of the present invention being cytoprotective agents.

EXAMPLES

The compounds used in the process of the present invention may be prepared by the general procedures disclosed in the literature, e.g. the procedures disclosed in U.S. Pat. Nos. 4,122,274 and 4,209,620.

Preparation of certain compounds included within the present invention has not specifically been disclosed in U.S. Pat. Nos. 4,122,274 and 4,209,620. While these compounds are prepared by known procedures, applicants have provided below suitable procedures for their preparation.

EXAMPLE 1

9-n-Propyl-3-(1H-tetrazol-5-yl)-4H-pyrido[1,2-a]-pyrimidin-4-one

A. 2-Amino-3-n-propylpyridine

The title compound was prepared by the direct amination of 3-n-propylpyridine by a method similar to that described for the preparation of 2-amino-3-ethylpyridine.[1] The initial mixture of 2-amino-3-n-propylpyridine and 2-amino-5-n-propylpyridine was separated by high pressure liquid chromatography. The 2-amino-3-n-propylpyridine was recrystallized from n-pentane to give material with m.p. 25°–27°.

Ref. No. 1. M. M. Robison and B. L. Robison, J. Amer. Chem. Soc. 77: 457 (1955).

B. Ethyl 2-cyano-3-(3-n-propyl-2-pyridylamino) acrylate

The title compound (m.p. 99°–100°, 60% yield) was prepared from 2-amino-3-n-propylpyridine and ethyl ethoxymethylenecyanoacetate in a manner similar to that described for the preparation of ethyl 2-cyano-3-(5-n-butyl-2-pyridylamino)acrylate in Preparation D3 of U.S. Pat. No. 4,122,274.

Anal. calcd for $C_{14}H_{17}N_3O_2$: C, 64.84; H, 6.61; N, 16.21. Found: C, 64.83; H, 6.61; N, 16.07.

C.
9-n-Propyl-3-(1H-tetrazol-5-yl)-4H-pyrido[1,2-a]pyrimidin-4-one

The title compound (m.p. 269°–272° with decomposition, 27.6% yield) was prepared from ethyl 2-cyano-3-(3-n-propyl-2-pyridylamino)acrylate in a manner similar to that described for the preparation of 3-(1H-tetrazol-5-yl)-4H-pyrido[1,2-a]pyrimidin-4-one in Example 2 of U.S. Pat. No. 4,122,274.

Anal. calcd for $C_{12}H_{12}N_6O$: C, 56.24; H, 4.72; N, 32.80. Found: C, 56.15; H, 4.64; N, 32.99.

EXAMPLE 2

9-n-Butyl-3-(1H-tetrazol-5-yl)-4H-pyrido[1,2-a]-pyrimidin-4-one

A. Ethyl 2-cyano-3-(3-n-butyl-2-pyridylamino)acrylate

The title compound (m.p. 98.5°–99.5°, 84% yield) was prepared from 2-amino-3-n-butylpyridine and ethyl ethoxymethylenecyanoacetate in a manner similar to that described for the preparation of ethyl 2-cyano-3-(5-n-butyl-2-pyridylamino)acrylate in Preparation 3D of U.S. Pat. No. 4,122,274.

Anal. calcd for $C_{15}H_{19}N_3O_2$: C, 65.91; H, 7.01; N, 15.37. Found: C, 65.73; H, 6.95; N, 15.32.

B. 9-n-Butyl-3-(1H-tetrazol-5-yl)-4H-pyrido[1,2-a]pyrimidin-4-one

The title compound (m.p. 255.5°–257.5° with decomposition, 30% yield) was prepared from ethyl 2-cyano-3-(3-n-butyl-2-pyridylamino)acrylate in a manner similar to that described for the preparation of 3-(1H-tetrazol-5-yl)-4H-pyrido[1,2-a]pyrimidin-4-one in Example 2 of U.S. Pat. No. 4,122,274.

Anal. calcd for $C_{13}H_{14}N_6O$: C, 57.76; H, 5.22; N, 31.10. Found: C, 57.71; H, 5.32; N, 31.07.

EXAMPLE 3

9-Chloro-3-(1H-tetrazol-5-yl)-4H-pyrido[1,2-a]-pyrimidin-4-one

A. Ethyl 2-cyano-3-(3-chloro-2-pyridylamino)acrylate

The title compound (m.p. 139.5°–141.5°, 44% yield) was prepared from 2-amino-3-chloropyridine and ethyl ethoxymethylenecyanoacetate in a manner similar to that described for the preparation of ethyl 2-cyano-3-(5-n-butyl-2-pyridylamino)acrylate in Preparation D3 of U.S. Pat. No. 4,122,274.

Anal. calcd for $C_{11}H_{10}ClN_3O_2$: C, 52.50; H, 4.01; Cl, 14.09; N, 16.70. Found: C, 52.22; H, 3.98; Cl, 13.93; N, 17.07.

B. 9-Chloro-3-(1H-tetrazol-5-yl)-4H-pyrido[1,2-a]pyrimidin-4-one

The title compound (m.p. 313°–315° with decomposition, 44% yield) was prepared from ethyl 2-cyano-3-(3-chloro-2-pyridylamino)acrylate in a manner similar to that described for the preparation of 3-(1H-tetrazol-5-yl)4H-pyrido[1,2-a]pyrimidin-4-one in Example 2 of U.S. Pat. No. 4,122,274.

We claim:

1. A method of inducing cytoprotective activity in a mammalian host in need of such treatment, which comprises administering to said host a cytoprotective dose of a compound of the formula

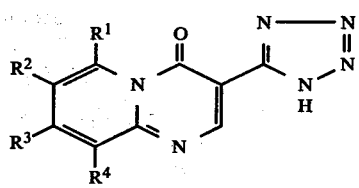

wherein $R^1$, $R^2$, $R^3$ and $R^4$ which may be the same or different are each hydrogen, halogen or (lower)alkyl, or wherein $R^3$ or $R^4$ when taken together are $$(CH_2)_n$$

in which n is 3, 4 or 5, or a pharmaceutically acceptable salt thereof, with the proviso that $R^1$, $R^2$, $R^3$ and $R^4$ may not all be hydrogen.

2. A method of inducing cytoprotective activity in a mammalian host in need of such treatment, which comprises administering to said host a cytoprotective dose of a compound of the formula

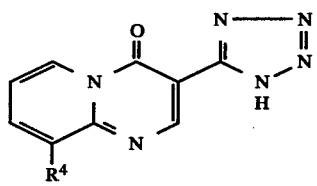

wherein $R^4$ is halogen or (lower)alkyl.

3. The method of claim 2 wherein $R^4$ is chloro.
4. The method of claim 2 wherein $R^4$ is methyl.
5. The method of claim 2 wherein $R^4$ is ethyl.
6. The method of claim 2 wherein $R^4$ is n-propyl.
7. The method of claim 2 wherein $R^4$ is n-butyl.

8. A method of inducing cytoprotective activity in a mammalian host in need of such treatment, which comprises administering to said host a cytoprotective dose of a compound of the formula

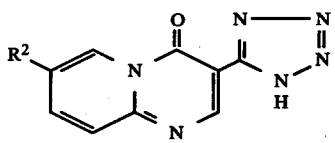

wherein $R^2$ is halogen or (lower)alkyl.

9. The method of claim 8 wherein $R^2$ is chloro.
10. The method of claim 8 wherein $R^2$ is methyl.
11. The method of claim 8 wherein $R^2$ is ethyl.
12. The method of claim 8 wherein $R^2$ is n-butyl.

13. A method of inducing cytoprotective activity in a mammalian host in need of such treatment, which comprises administering to said host a cytoprotective dose of a compound of the formula

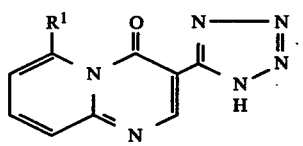

wherein $R^1$ is halogen or (lower)alkyl.

14. The method of claim 13 wherein $R^1$ is methyl.

15. A method of inducing cytoprotective activity in a mammalian host in need of such treatment, which comprises administering to said host a cytoprotective dose of a compound of the formula

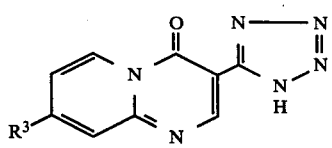

wherein R³ is halogen or (lower)alkyl.

16. The method of claim 15 wherein R³ is methyl.

17. A method of inducing cytoprotective activity in a mammalian host in need of such treatment, which comprises administering to said host a cytoprotective dose of a compound of the formula

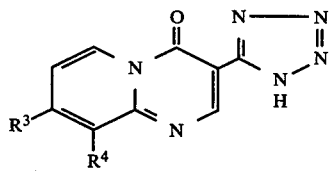

wherein R³ and R⁴ when taken together represent $(CH_2)_n$ in which n is 3, 4 or 5.

18. The method of claim 17 wherein R³ and R⁴ are —(CH₂)₄.

19. A method of inducing cytoprotective activity in a mammalian host in need of such treatment, which comprises administering to said host a cytoprotective dose of a compound of the formula

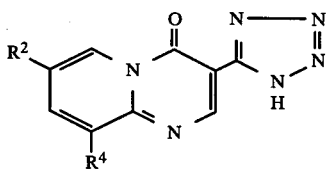

wherein R² and R⁴ are each independently (lower)alkyl.

20. The method of claim 19 wherein R² and R⁴ are both methyl.

* * * * *